United States Patent [19]

Ohmori et al.

[11] Patent Number: 4,564,717

[45] Date of Patent: Jan. 14, 1986

[54] FLUORINE-CONTAINING OLEFIN

[75] Inventors: Akira Ohmori, Ibaraki; Nobuyuki Tomihashi, Takatsuki; Hiroshi Inukai; Yoshiki Shimizu, both of Settsu, all of Japan

[73] Assignee: Daikin Kogyo Co., Ltd., Osaka, Japan

[21] Appl. No.: 653,006

[22] Filed: Sep. 21, 1984

[30] Foreign Application Priority Data

Sep. 21, 1983 [JP] Japan ................................. 58-175122

[51] Int. Cl.[4] ........................ C07C 33/42; C08F 12/20
[52] U.S. Cl. .................................... 568/843; 526/242; 526/249; 526/250
[58] Field of Search ................................. 568/843, 845

[56] References Cited

U.S. PATENT DOCUMENTS 3,483,263  12/1969  Schlechting et al. ................ 568/843

OTHER PUBLICATIONS

Kainov et al., C. A., 79, 1973, 53568d, USSR, 375,298.

*Primary Examiner*—Howard T. Mars
*Attorney, Agent, or Firm*—Armstrong, Nikaido, Marmelstein & Kubovcik

[57] ABSTRACT

A fluorine-containing olefin of the formula: $CF_2=CF(CF_2)_m(CH_2)_nOH$ wherein m is 0 or an integer of 1 to 10 and n is an integer of 1 to 4, which is copolymerizable with various ethylenically unsaturated compounds and provide fluorine-containing copolymers useful as raw materials for room temperature curing paints, fluorine-containing rubbers and the like.

1 Claim, No Drawings

FLUORINE-CONTAINING OLEFIN

BACKGROUND OF THE INVENTION

The present invention relates to a novel fluorine-containing olefin, and more particularly to a novel fluorine-containing olefin useful as a monomeric material for preparing fluorine-containing polymers.

It is an object of the present invention to provide a novel fluorine-containing olefin.

A further object of the present invention is to provide a novel fluorine-containing olefin having a functional group.

A still further object of the present invention is to provide a novel fluorine-containing olefin which is co-polymerizable with ethylenically unsaturated compounds and provide fluorine-containing copolymers useful as raw materials for paints and fluororubbers curable at room temperature.

These and other objects of the present invention will become apparent from the description hereinafter.

SUMMARY OF THE INVENTION

In accordance with the present invention, there is provided a fluorine-containing olefin of the formula:

$$CF_2=CF(CF_2)_m(CH_2)_nOH$$

wherein m is 0 or an integer of 1 to 10 and n is an integer of 1 to 4.

The fluorine-containing olefins of the present invention are copolymerizable with ethylenically unsaturated compounds such as ethylene and propylene, and ethylenically unsaturated fluorine-containing compounds such as tetrafluroethylene, chlorotrifluoroethylene and 1,1-difluoroethylene. The copolymers of the fluorine-containing olefin of the invention and other olefins can be utilized as raw materials for room temperature curing fluoro-resin paints and fluoro-rubbers.

DETAILED DESCRIPTION

The novel fluorine-containing olefin of the present invention having the formula (1):

$$CF_2=CF(CF_2)_m(CH_2)_nOH \tag{1}$$

wherein m is 0 or an integer of 1 to 10 and n is an integer of 1 to 4, can be synthesized, for instance, by preparing a compound of the formula (2):

$$CF_2X^1CFX^2(CF_2)_m(CH_2)_nOH \tag{2}$$

wherein $X^1$ and $X^2$ are the same or different and each is chlorine or bromine, and m and n are as defined above, and causing chlorine and/or bromine to eliminate from the compound (2).

The compound (2) can be prepared by various processes, for instance, by the following processes (a), (b) and (c).

(a) The compound (2) is prepared by reducing a compound of the formula (3):

$$CF_2X^1CFX^2CF_2COOR \tag{3}$$

wherein $X^1$ and $X^2$ are as defined above, and R is a lower aliphatic group or an alicyclic group, with a reducing agent as used in a usual reduction reaction, e.g. hydrogen (used with a catalyst such as platinum oxide or palladium), lithium aluminum hydride, sodium borohydride or lithium borohydride. The reaction is carried out in a solvent such as water, ethers or alcohols at a temperature of 5° to 100° C., usually at a reflux temperature of the reaction solvent used. Examples of the solvent are, for instance, diethyl ether, dibutyl ether, tetrahydrofuran, dioxane, N-methylmorpholine, methanol, and the like. In case of using hydrogen as a reducing agent, the reaction pressure is usually from 1 to 150 atms, and in case of other reducing agents, the reaction is conducted at atmospheric pressure. The amount of the reducing agent is from a stoichiometric amount to 10 times the stoichiometric amount.

(b) In another process for preparing the compound (2), a compound of the formula (4):

$$CF_2X^1CFX^2(CF_2)_mI \tag{4}$$

wherein $X^1$, $X^2$ and m are as defined above, is reacted with ethylene by using a radical-producing compound, e.g. peroxides and azo compounds, as a catalyst, by ultraviolet radiation, or by heating, to generate iodine radical, thereby producing a compound of the formula: $CF_2X^1CFX^2(CF_2)_mCH_2CH_2I$ wherein $X^1$, $X^2$ and m are as defined above. A reaction solvent such as a halogenated hydrocarbon or water may be employed. The compound (2) is obtained by reacting the thus produced compound with chlorosulfonic acid and water in that order. In this oxidation reaction, a reaction solvent such as a halogenated hydrocarbon may be employed. Examples of the peroxides are, for instance, t-butyl peroxyisobutyrate, t-butylperoxy(2-ethylhexanoate), isobutyryl peroxide and di-isopropyl peroxydicarbonate. Examples of the azo compounds are, for instance, azobisisobutyronitrile. Both the above-mentioned former ethylene addition reaction and latter oxidation reaction are conducted at a temperature of 15° to 200° C. The reaction pressure is from 1 to 50 atms for the ethylene addition reaction and from 1 to 10 atms for the oxidation reaction.

(c) The compound (2) is also prepared by subjecting the compound (4) and allyl alcohol to a radical reaction in the same manner as in the above process (b) to produce a compound of the formula: $CF_2X^1CFX^2(CF_2)_mCH_2CHICH_2OH$ wherein $X^1$, $X^2$ and m are as defined above, and then reducing the resulting compound. The former reaction is carried out usually at a temperature of 15° to 150° C. and a pressure of 1 to 10 atms. The latter reduction reaction can be conducted in the same manner as in the process (a).

The compound (2) as obtained by the above processes (a), (b) and (c) is reacted with a dehalogenation agent such as zinc, magnesium, tin, sodium or potassium to eliminate chlorine and/or bromine. The reaction is carried out at a temperature of 0° to 150° C., preferably 50° to 100° C., at a pressure of 1 to 10 atms in a reaction solvent such as water, dimethylformamide, methanol or acetone.

The present invention is more specifically described and explained by means of the following Examples. It is to be understood that the present invention is not limited to the Examples, and various changes and modifications may be made in the invention without departing from the spirit and scope thereof.

EXAMPLE 1

[Synthesis of $CF_2=CFCH_2CH_2OH$]

(1) A liter autoclave equipped with a stirrer and a thermometer was charged with 1 mole (279 g) of $CF_2ClCFClI$ and 3 g of t-butyl peroxyisobutyrate. After degassing, ethylene was supplied to the autoclave and the reaction was carried out at a temperature of 70° to 80° C., while maintaining the inner pressure at 5 kg/cm²G with supply of ethylene, until no ethylene was consumed. The reaction mixture was taken out and was rectified, thus $CF_2ClCFClCH_2CH_2I$ (boiling point: 68° to 70° C. at 25 mmHg) was obtained in a yield of 96%.

(2) A 1 liter flask equipped with a stirrer and a thermometer was charged with 0.5 mole (151.5 g) of $CF_2ClCFClCH_2CH_2I$ and 1 mole (116.5 g) of chlorosulfonic acid, and the reaction was carried out at 40° C. for 24 hours. The obtained reaction mixture was added dropwise to water, and the under oil layer was taken out and rectified to give 82 g of $CF_2ClCFClCH_2CH_2OH$ (yield: 83.7%).

(3) A 1 liter flask equipped with a stirrer, a thermometer, a reflux condenser and a dropping funnel was charged with 300 ml of water and 100 g of zinc, and 0.5 mole (98.5 g) of $CF_2ClCFClCH_2CH_2OH$ was added dropwise to the flask at a temperature of 50° to 60° C. The inner temperature rose to 80° C. by heat generation with start of the reaction. After the completion of the dropwise addition, the reaction was continued at 80° C. for 5 hours. The obtained organic compound was rectified to give $CF_2=CFCH_2CH_2OH$ (boiling point: 93° C. at 760 mmHG). The yield throughout the steps (1) to (3) was 73%.

The obtained product was subjected to nuclear magnetic resonance (NMR) analysis. The results are shown below.

NMR data in which fluorine atom and hydrogen atom are indicated as follows:

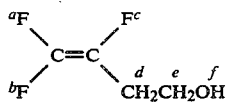

| $^{19}F$ (external standard: $CF_3COOH$, high magnetic field side: +, hereinafter the same) | | |
|---|---|---|
| Fluorine atom | +δ (ppm) | Spin-spin bond (Hz) |
| a | 26.9 | d, d, t, $J_{gem}$ = 89, $J_{cis}$ = 34, $J_{F-H}$ = 2 |
| b | 47.0 | d, d, t, $J_{trans}$ = 114, $J_{gem}$ = 89, $J_{F-H}$ = 4 |
| c | 97.8 | d, d, t, $J_{cis}$ = 34, $J_{trans}$ = 114, $J_{F-H}$ = 21 |

| $^{1}H$ (internal standard: tetramethylsilane, hereinafter the same) | | |
|---|---|---|
| Hydrogen atom | δ (ppm) | Spin-spin bond (Hz) |
| d | 2.57 | d, m, $J_{F-H}$ = 21 |
| e | 3.83 | t, $J_{H-H}$ = 7 |
| f | 4.4 | s |

EXAMPLE 2

[synthesis of $CF_2=CFCF_2CF_2CH_2CH_2OH$]

A 1 liter autoclave equipped with a stirrer and a thermometer was charged with 1 mole (279 g) of $CF_2ClCFClI$, 5 g of t-butyl peroxyisobutyrate and 100 g of water. After degassing, tetrafluoroethylene was supplied to the autoclave and the reaction was carried out at a temperature of 70° to 80° C., while maintaining the inner pressure at 3 kg/cm²G with supply of tetrafluroethylene. After the completion of the supply of 1 mole of tetrafluroethylene, the reaction mixture was allowed to stand for some time and the reaction was finished. The reaction mixture was rectified. Employing the thus obtained product, the desired compound $CF_2=CFCF_2CF_2CH_2CH_2OH$ was prepared in the same manner as in the steps (2) and (3) of Example 1. The boiling point of the final product was 107° C. at 200 mmHg, and the yield throughout the whole reactions was 77%.

The results of NMR analysis are shown below.

NMR data in which fluorine atom and hydrogen atom are indicated as follows:

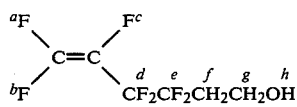

| $^{19}F$ | | |
|---|---|---|
| Fluorine atom | +δ (ppm) | Spin-spin bond (Hz) |
| a | 14 | d, d, t, $J_{gem}$ = 60, $J_{cis}$ = 40, $J_{F-F}$ = 6 |
| b | 30.3 | d, d, t, t, $J_{trans}$ = 116, $J_{gem}$ = 60, $J_{F-F}$ = 28.5 |
| c | 111.4 | d, d, m, $J_{trans}$ = 116, $J_{cis}$ = 40, |
| d | 42.7 | m |
| e | 37.8 | t, m, $J_{F-H}$ = 18 |

| $^{1}H$ | | |
|---|---|---|
| Hydrogen atom | δ (ppm) | Spin-spin bond (Hz) |
| f | 2.4 | t, t, $J_{F-H}$ = 18, $J_{H-H}$ = 7 |
| g | 3.9 | t, $J_{H-H}$ = 7 |
| h | 4.6 | s |

EXAMPLE 3

[Synthesis of $CF_2=CFCF_2CH_2OH$]

A 1 liter flask equipped with a stirrer, a thermometer, a reflux condenser and a dropping funnel was charged with 5.5 g of $LiAlH_4$. After replacing air in the flask with nitorgen, 200 ml of diethyl ether was added dropwise to the flask through the dropping funnel. Thereafter, 200 ml of a diethyl ether solution of 0.1 mole (26.1 g) $CF_2ClCFClCF_2COOCH_3$ was added dropwise to the flask through the dropping funnel over about 2 hours with stirring, and diethyl ether was then refluxed for about 15 minutes under heating.

The reaction mixture was cooled to room temperature, and water was added to the flask to decompose the unreacted $LiAlH_4$. The reaction mixture was then acidified with diluted hydrochloric acid. An organic layer was taken out, and rectified to isolate CF$_2$ClCFClCF$_2$CH$_2$OH (boiling point: 85° C. at 30 mmHg). The yield was 85%.

Dechlorination reaction was then carried out in the same manner as in the step (3) of Example 1 to give CF$_2$=CFCF$_2$CH$_2$OH (boiling point: 96° C. at 760 mmHg). The yield throughout the whole reactions was 70%.

The results of NMR analysis are shown below.

NMR data in which fluorine atom and hydrogen atom are indicated as follows:

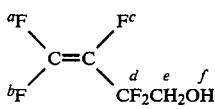

| Fluorine atom | $^{19}F$ +δ (ppm) | Spin-spin bond (Hz) |
|---|---|---|
| a | 18.8 | d, d, t, $J_{gem}$ = 68, $J_{cis}$ = 37, $J_{F-F}$ = 6 |
| b | 33 | d, m, $J_{trans}$ = 13 |
| c | 112.5 | d, d, m, $J_{cis}$ = 37, $J_{trans}$ = 113, |
| d | 35.1 | m |

| Hydrogen atom | $^{1}H$ δ (ppm) | Spin-spin bond (Hz) |
|---|---|---|
| e | 4.0 | t, $J_{H-F}$ = 115 |
| f | 4.7 | s |

EXAMPLE 4

[Synthesis of CF$_2$=CFCH$_2$CH$_2$CH$_2$OH]

A 1 liter flask equipped with a stirrer, a thermometer, a reflux condenser and a dropping funnel was charged with 279 g of CF$_2$ClCFCll and 3.5 g of azobisisobutyronitrile. After heating to 90° C. with stirring, 75 g of allyl alcohol was added dropwise to the flask through the dropping funnel. The reaction was further continued at a temperature of 90° to 95° C. for 15 hours. The unreacted starting material was removed from the reaction mixture under reduced pressure to give 303 g of CF$_2$ClCFClCH$_2$CHlCH$_2$OH.

To the above product were added 500 ml of diethyl ether and 25 g of LiAlH$_4$, and the reduction reaction was carried out under reflux of diethyl ether to give 125 g of CF$_2$ClCFClCH$_2$CH$_2$CH$_2$OH. The yield was 65%.

Dechlorination reaction was then carried out in the same manner as in the step (3) of Example 1 to give CF$_2$=CFCH$_2$CH$_2$CH$_2$OH (boiling point: 95° C. at 155 mmHg). The yield throughout the whole reactions was 55%.

The results of NMR analysis are shown below.

NMR data in which fluorine atom and hydrogen atom are indicated as follows:

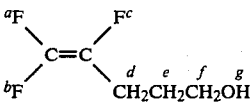

| Fluorine atom | $^{19}F$ +δ (ppm) | Spin-spin bond (Hz) |
|---|---|---|
| a | 29.9 | d, d, t, $J_{gem}$ = 92, $J_{cis}$ = 33, $J_{H-F}$ = 2 |
| b | 48.5 | d, d, t, $J_{trans}$ = 116, $J_{gem}$ = 92, $J_{H-F}$ = 4 |
| c | 97.5 | d, d, t, $J_{trans}$ = 116, $J_{cis}$ = 33, $J_{F-H}$ = 22 |

| Hydrogen atom | $^{1}H$ δ (ppm) | Spin-spin bond (Hz) |
|---|---|---|
| d | 2.6 | d, m, $J_{F-H}$ = 22 |
| e | 2.05 | q, $J_{H-H}$ = 7 |
| f | 3.86 | t, $J_{H-H}$ = 7 |
| g | 5.33 | s |

EXAMPLE 5

A 1 liter glass autoclave was charged with 400 g of tetrafluorodichloroethane, 250 ml of water, 2 g of diisobutyryl peroxide and 5.5 g of the monomer synthesized in Example 2. After degassing, a monomer mixture of 1,1-difluoroethylene and chlorotrifluoroethylene in a molar ratio of 9:1 was supplied to the autoclave, and the polymerization was carried out at 40° C. for 21 hours with stirring, while maintaining the pressure at 8 kg/cm$^2$ with supply of the monomer mixture and adding 1 g of di-isobutyryl peroxide and 5 g of the monomer synthesized in Example 2 every 5 hours. The pressure is released, and the reaction mixture was taken out, washed with water and dried at 80° C. to give 85 g of a copolymer.

In 70 g of isobutyl acetate was dissolved 30 g of the copolymer, and 13 g of hexamethylene diisocyanate trimer was added to the solution. The solution was cast onto an aluminum plate and cured. The cured film was transparent and glossy and had a pencil hardness of 2H. The film was also subjected to an accelerated weathering test by Weather-O-Meter for 4,000 hours, but there was little change and the film had a very excellent weatherability as compared with a polymethyl methacrylate film tested simultaneously.

In addition to the ingredients used in the Examples, other ingredients can be used in the Examples as set forth in the specification to obtain substantially the same results.

What we claim is:
1. A fluorine-containing olefin of the formula:

CF$_2$=CF(CF$_2$)$_m$(CH$_2$)$_n$OH wherein m is an integer of 1 to 10 and n is an integer of 1 to 4.

* * * * *